United States Patent
Vincent

(10) Patent No.: US 12,070,426 B2
(45) Date of Patent: Aug. 27, 2024

(54) AIR CONDITIONING ASSEMBLY

(71) Applicant: Sporting Edge (UK) Ltd., Basingstoke (GB)

(72) Inventor: David Vincent, Sherfield on Loddon (GB)

(73) Assignee: Sporting Edge (UK) Ltd., Hampshire (GB)

( * ) Notice: Subject to any disclaimer, the term of this patent is extended or adjusted under 35 U.S.C. 154(b) by 0 days.

(21) Appl. No.: 18/275,352

(22) PCT Filed: Feb. 3, 2022

(86) PCT No.: PCT/EP2022/052550
§ 371 (c)(1),
(2) Date: Aug. 1, 2023

(87) PCT Pub. No.: WO2022/167509
PCT Pub. Date: Aug. 11, 2022

(65) Prior Publication Data
US 2024/0091088 A1    Mar. 21, 2024

(30) Foreign Application Priority Data
Feb. 3, 2021 (GB) ...................... 2101483

(51) Int. Cl.
*A61G 10/02* (2006.01)
*F24F 3/14* (2006.01)
(Continued)

(52) U.S. Cl.
CPC ............. *A61G 10/023* (2013.01); *F24F 3/14* (2013.01); *F24F 2110/10* (2018.01); *F24F 2110/20* (2018.01); *F24F 2110/76* (2018.01)

(58) Field of Classification Search
CPC ...... A61G 10/023; A61G 10/04; A61G 10/02; A61G 10/005; A61G 13/108; B64D 13/06;
(Continued)

(56) References Cited

U.S. PATENT DOCUMENTS

| | | | | |
|---|---|---|---|---|
| 3,143,952 A | * | 8/1964 | Simons | F24F 9/00 |
| | | | | 454/190 |
| 4,838,150 A | * | 6/1989 | Suzuki | F24F 3/167 |
| | | | | 55/385.2 |

(Continued)

FOREIGN PATENT DOCUMENTS

| | | | |
|---|---|---|---|
| WO | 9703631 A1 | 2/1997 | |
| WO | WO-2015107714 A1 * | 7/2015 | .............. F24F 13/02 |

OTHER PUBLICATIONS

English Machine Translation of WO 2015107714 A1 provided by Espacenet (Year: 2015).*

(Continued)

*Primary Examiner* — Joseph D. Boecker
*Assistant Examiner* — Brian T Khong
(74) *Attorney, Agent, or Firm* — Christopher M. Ramsey; GrayRobinson, P.A.

(57) ABSTRACT

An air conditioning assembly for an environmental chamber includes an air handling unit for supplying air to the environmental chamber. A plurality of ducts in fluid communication with the air handing unit and in fluid communication with the environmental chamber are configured to draw air from one side of the environmental chamber through at least one outlet vent, and to blow air into an opposite side of the environmental chamber through at least one equal but opposite inlet vent. At least one air conditioning means in fluid communication with the at least one air handling unit is configured to condition the air flow passing through the air handling unit. The at least one air conditioning means (Continued)

includes an altitude simulator for changing the oxygen content of the air flow. In use, the air conditioning assembly is configured to create substantially laminar air flow throughout the environmental chamber.

14 Claims, 3 Drawing Sheets

(51) Int. Cl.
*F24F 110/10* (2018.01)
*F24F 110/20* (2018.01)
*F24F 110/76* (2018.01)

(58) Field of Classification Search
CPC ........... B64D 13/08; B64D 2013/0603; B64D 2013/0625; B64D 2013/0651; B64D 2013/0655; B64D 2013/0662; B64D 2013/0681; B64D 2013/0685; B64D 2013/0688; A61B 5/6888; A62B 31/00; A63B 2213/006; A63B 2213/005; A63B 23/18; E04H 3/08; F24F 3/167; F24F 3/16; F24F 3/163; F24F 3/14; F24F 3/044; F24F 7/04; F24F 7/06; A61M 16/10

See application file for complete search history.

(56) References Cited

U.S. PATENT DOCUMENTS

| | | | |
|---|---|---|---|
| 6,626,971 B1 * | 9/2003 | Forbert | F24F 9/00 55/385.2 |
| 10,190,784 B1 * | 1/2019 | Rue | F24F 13/0254 |
| 2019/0328595 A1 * | 10/2019 | Vincent | F24F 1/0047 |
| 2020/0155999 A1 | 5/2020 | Vincent | |

OTHER PUBLICATIONS

International Search Report of May 30, 2022 for PCT/EP2022/052550.

* cited by examiner

AIR CONDITIONING ASSEMBLY

CROSS-REFERENCE TO RELATED APPLICATIONS

This is the U.S. National Stage application of International Application No. PCT/EP2022/052550, filed Feb. 3, 2022, which claims the benefit of priority from GB 2101483.2, filed Feb. 3, 2021. The entire contents of the prior applications are incorporated by reference herein.

FIELD

This invention pertains generally to the field of air conditioning assemblies for environmental chambers, and in particular means of converting a room to form an environmental chamber.

BACKGROUND

Environmental chambers typically comprise an enclosed space within which specific environmental conditions can be controlled, varied and monitored. Test subjects are placed within the chamber, and their performance tracked when subjected to a change in conditions. The temperature and humidity of the air in the environmental chamber may be varied. There may also be a requirement to simulate altitude within the chamber, in order to establish particular stress conditions and impose these upon the test subjects. There are a number of uses for such chambers, including, but not limited to, medical or scientific research, materials research, the improvement of human or animal performance and assisting rehabilitation during injury recovery.

A typical example of an altitude simulator is a hypoxic generator. These are used during hypoxic therapy by individuals to obtain the benefits in physical performance and wellbeing through improved oxygen metabolism. A hypoxic generator is a device that is used to deprive the body of a normal oxygen supply. These generators comprise apparatus to provide reduced oxygen, or hypoxic air to a user for active or passive simulated altitude training. Hypoxic air typically contains less than 21% oxygen concentration.

Incorporating some element of exposure to reduced oxygen atmospheres into a training program can be beneficial in terms of performance and general wellbeing. It has become a widely used element of training for elite athletes and is starting to become used by amateurs. Key uses might include pre-acclimatisation before travelling to high altitude climates, assisting with weight loss and for maintaining fitness levels when suffering from injury.

Typically, the aim is for the entire volume of the chamber to experience the same climatic conditions at any one time. Conditions such as temperature, humidity, oxygen level and wind chill can be varied and monitored, allowing proper evaluation and comparisons of those subjects contained within the chamber to be made and conclusions reached. Uniformity of these variable conditions throughout the chamber is required for an effective test to be conducted. However, with the existing systems that are currently used to form environmental chambers, this uniformity is very difficult to achieve. More often than not the chamber has zones that are at the required condition, but pockets that are experiencing very different conditions.

Environmental chambers typically require numerous devices to be able to create the variable conditions. These devices are often required to cool, heat, humidify, dehumidify the air flow, and vary the oxygen concentration of the air flow passing therethrough. They also require numerous sensors to monitor conditions and ensure that predetermined values are met. When mounted in an environmental chamber, all of this equipment can cause clutter within the chamber itself, and is often visually unattractive. It also inevitably creates the localised climatic pockets as previously described.

An alternative approach has been to house all climate controlling devices outside of the chamber, and connecting these with the chamber through ductwork. This approach would often require an Air Handling Unit, or AHU. This air handling unit would typically comprise a cooling coil, dehumidification device, heaters and a humidifier. Air with reduced, or enhanced, oxygen content can also be introduced into the AHU, or through the ductwork, again creating localised conditions that are often different at the entrance points, exit points and other locations within the chamber.

Both of these arrangements of environmental chamber have a common disadvantage, namely a poor uniformity of conditions throughout the chamber, which makes proper scientific measurements difficult and, if used for performance, delivers different training environments to athletes exercising within the space. Those near air flow outlet points will experience a different wind chill, and therefore different temperatures and humidity, to those positioned near air flow return points, who will in turn get different conditions to those centrally located within the chamber.

There is a need to improve the uniformity of environmental conditions throughout the environmental chamber, without impacting upon the test subjects making use of the chamber. There is a need to create an effective laminar air flow throughout the chamber, whilst also providing an assembly for converting a room to become an environmental chamber. There is a need to be able to convert an existing room to become an environmental chamber, where headroom is limited, and without required considerable alterations to the building infrastructure. There is also an advantage to removing any clutter from such an environmental chamber in order to maximise the space and improve aesthetics and to remove maintenance activities from having to take place in the chamber itself.

The prior art shows a number of devices which attempt to address these needs in various ways.

WO 2016 098 598 (Fuji Medical Science Company Limited) discloses an artificial environmental control chamber for sports science use, that is configured to test the influence of a low-temperature and low-humidity environment on a body. An air blowing device blows air into the test chamber and a cylindrical air ventilation duct is disposed within an upper part of the chamber to assist with air circulation. Whilst providing additional means to improve air flow and uniformity of conditions throughout the chamber, there is still likely to be variation across the chamber. The devices also cause clutter within the test space.

GB 2 558 625 (Sporting Edge UK Limited) discloses an air conditioning assembly for an environmental chamber where a suspended ceiling is installed leaving a perimeter gap at either end. This set-up requires the air conditioning equipment to be housed within the headspace of the room, behind the suspended ceiling. Whilst this produces the desirable substantially laminar flow and uniformity of environment, this headroom is not always available

BRIEF SUMMARY

Whilst the prior art appears to address the issue of improving air flow in an environmental chamber by improving air circulation within the chamber, this does not create a laminar flow of air across the chamber, and therefore uniform conditions throughout the test space. This prior art does not address the issue of converting an existing room into an environmental chamber, where head room is limited, and with minimal alterations to the existing building infrastructure.

Preferred embodiments of the present invention aim to provide an air conditioning assembly to provide air conditioning means within a room, thus turning the room into an environmental chamber, and ensuring uniform environmental conditions throughout the environmental chamber, where head room is limited and with minimal changes to the building's infrastructure. In addition, embodiments of the present invention aim to provide a clutter-free, concealed solution when converting a room into an environmental chamber.

According to one aspect of the present invention, there is provided an air conditioning assembly for an environmental chamber, the air conditioning assembly comprising: an air handling unit for supplying air to the environmental chamber; a plurality of ducts in fluid communication with the air handing unit and in fluid communication with the environmental chamber; the ducts being configured to draw air from one side of the environmental chamber through at least one outlet vent, and to blow air into an opposite side of the environmental chamber through at least one equal but opposite inlet vent; and, at least one air conditioning means in fluid communication with the at least one air handling unit, configured to condition the air flow passing through said air handling unit; wherein, the at least one air conditioning means comprises an altitude simulator for changing the oxygen content of the air flow, and whereby, in use, the air conditioning assembly is configured to create substantially laminar air flow throughout the environmental chamber.

Preferably, the plurality of ducts may comprise an inlet duct trunk operatively connected to one end of a plurality of inlet duct pipes, whereby each inlet duct pipe comprises an inlet vent at their other end.

Preferably, the plurality of ducts may comprise an outlet duct trunk operatively connected to one end of a plurality of outlet duct pipes, whereby each outlet duct pipe comprises an outlet vent at their other end.

The air conditioning means may comprise a dehumidifier for reducing the humidity of the air flow.

The air conditioning means may comprise a humidifier for increasing the humidity of the air flow.

The air conditioning means may comprise a heater to increase the temperature of the air flow.

The air conditioning means may comprise a cooling radiator to reduce the temperature of the air flow.

Preferably, the air conditioning assembly may comprise one or more from the following list of sensors: oxygen sensor, temperature sensor, humidity sensor, carbon dioxide sensor.

The air conditioning assembly may comprise at least one control means operatively connected to the air handling unit and the at least one air conditioning means.

The air conditioning assembly may comprise at least one control means operatively connected to the sensors.

The air handling unit may comprise a cooling coil.

The air conditioning assembly may comprise flow directing means.

The flow directing means may comprise curved ceiling coving.

The flow directing means may comprise planar, inclined coving.

The air conditioning assembly, in use, may comprise outlet vents spaced equidistance from one another along one side of the environmental chamber, and inlet vents spaced equidistance from one another along an opposite side of the environmental chamber, such that the outlet vents mirror the inlet vents.

According to a further aspect of the present invention, there is provided an environmental chamber incorporating the air conditioning assembly of any one of the preceding claims.

According to yet a further aspect of the present invention, there is provided a method of installing the air conditioning assembly in a room to form an environmental chamber, comprising the steps of: mounting an air handling unit outside the environmental chamber; installing a plurality of ducts in fluid communication with the air handling unit and in fluid communication with the environmental chamber, the ducts being configured to draw air from one side of the chamber through at least one outlet vent, and to blow air into an opposite side of the environmental chamber through at least one equal but opposite inlet vent; and, installing at least one air conditioning means in fluid communication with the air handling unit, configured to condition the air flow passing through said air handling unit, wherein, the at least one air conditioning means comprises an altitude simulator for changing the oxygen content of the air flow, and whereby, in use, the air conditioning assembly is configured to create substantially laminar air flow throughout the environmental chamber.

BRIEF DESCRIPTION OF THE DRAWINGS

For a better understanding of the invention and to show how embodiments of the same may be carried into effect, reference will now be made, by way of example, to the accompanying diagrammatic drawings, in which.

In the figures like references denote like or corresponding parts.

DETAILED DESCRIPTION

Figure 1:
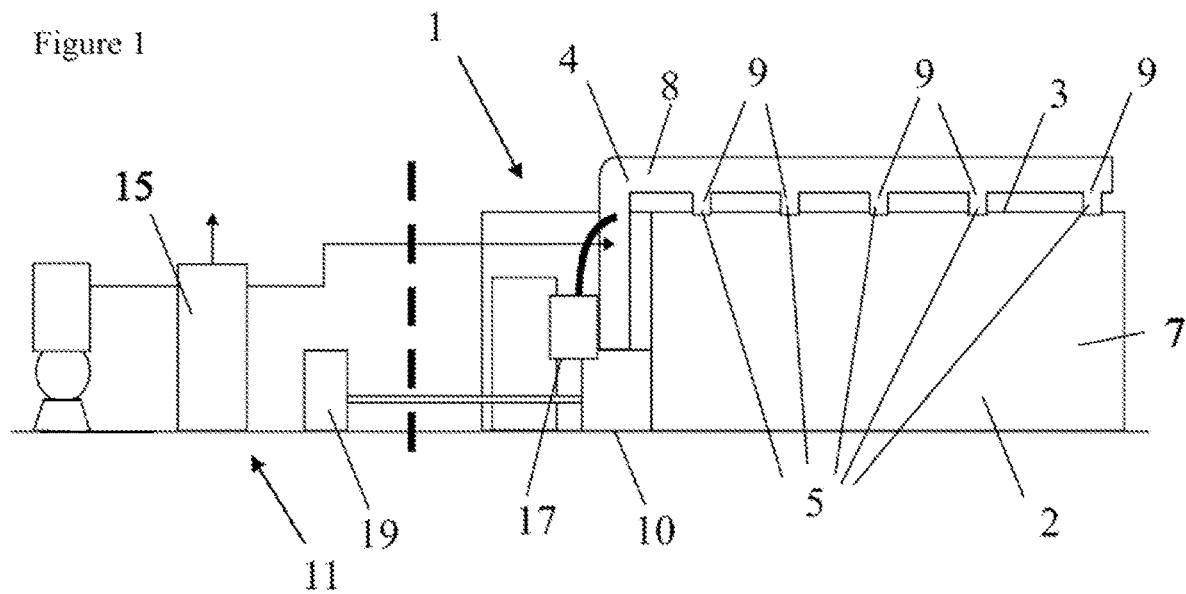
FIG. 1 shows one embodiment of air conditioning assembly in side view to create an environmental chamber, showing an air handling unit in conjunction with one or more air conditioning units, the air handling unit being operatively connected to an arrangement of duct work that supplies the chamber, creating substantially laminar air flow throughout the chamber.

FIG. 1 shows the air conditioning assembly 1 that is used to create the environmental chamber 2. The air conditioning assembly 1 comprises an air-handling unit 10, or AHU, installed outside the environmental chamber 2. An AHU 10 is an air handler, or a device used to regulate and circulate air as part of an air-conditioning system. AHUs 10 typically comprise a large metal box containing a blower or fan arrangement, heating and/or cooling elements, and various filter racks or chambers. AHUs 10 usually connect to a ductwork ventilation system that distributes the conditioned air through the building and returns it to the AHU 10. Sometimes AHUs 10 are configured to supply air and return air directly to and from the space served. The AHU 10 integrates the oxygen reduction/heating/cooling/humidification into a single air flow having the desired climatic and oxygen properties. The AHU 10 is operatively connected to a system of duct work 4 that feeds a plurality of inlet vents 5, each of which will deliver air with exactly the same climatic and oxygen properties as all other vents, and a plurality of outlet vents 6 within the ceiling 3 of the environmental chamber 2. In an alternative embodiment, not shown, the inlet vents 5 and outlet vents 6 may be installed within the walls 7. The aim of the duct work 4 is to distribute a flow of completely uniform air evenly within the environmental chamber 2, and ensure substantially laminar air flow is felt throughout the chamber, mitigating pockets of air and providing uniformity of climatic and oxygen content, with lack of wind chill, irrespective of the user location in the chamber.

The air handling unit 10 is operatively connected to at least one air conditioning means 11 to condition the air flow on route to the environmental chamber 2. The duct work 4 may comprise a duct trunk 8 that feeds a number of branches that lead off of it, or duct pipes 9. The duct pipes 9 comprise a much smaller diameter than the duct trunk 8. The duct pipes 9 are connected to the chamber through the inlet vents 5 and the outlet vents 6. These inlet vents 5 and outlet vents 6 may comprise the existing ceiling roses within the ceiling 3, or may be installed within the ceiling in order to create the environmental chamber 2 within the room. The inlet vents 5 and outlet vents 6 are spaced equidistance from one another, such that they span a length of the edge of the ceiling 3, with the inlet vents 5 and outlet vents 6 located opposite one another, such that they mirror each other. For every inlet vent 5 there is an equal but opposite outlet vent 6 on the opposite side of the room. It is this arrangement of duct work 4 and venting that creates the laminar air flow throughout the entire environmental chamber 2. An Air flow 12 can therefore travel between AHU 10 and environmental chamber 2 in a relatively unobstructed manner. The AHU 10 draws air from the environmental chamber 2 through the outlet vents 6, and supplies air to the environmental chamber 2 through the inlet vents 5. The AHU 10 provides flow control means for varying the rate of flow of the air flow 12 flowing through the environmental chamber 2.

An air conditioning means 11 is in fluid communication with the AHU 10, such that the air conditioning means 11 can alter the air flow 12 in a required way. The air conditioning means 11 is configured according to the requirements of the environmental chamber 2. The air conditioning means 11 may be configured to be mounted outside the environmental chamber 2 and alongside the AHU 10, or it may be situated within the environmental chamber 2, although still being operatively connected to the AHU 10.

The air conditioning means 11 may comprise one or more of the following items: an altitude simulator 15, a dehumidifier 16, a humidifier 17, a heater 18, a cooling radiator 19. The air conditioning means 11 may comprise any one of this list of items, or more than one of each of the items, or any combination of this list of items, again as singles or multiples depending on the specific requirements of the environmental chamber 2. The air conditioning means 11 may be provided as a modular arrangement of component items that are all configured to act upon the same air flow 12. The air conditioning means 11, with or without the AHU 10, may be contained within a housing, not shown.

The altitude simulator 15 is configured to provide a hypoxic or hyperoxic air flow 12 to the test space. The altitude simulator provides a variable injection of oxygen to the air flow 12 for reducing or increasing the simulated altitude experienced by test subjects within the environmental chamber 2.

The air conditioning means 11 provides environmental control devices to the environmental chamber 2. These environmental control devices simulate altitude, provide relative humidity and variable temperature of air flow 12 through the environmental chamber 2. The dehumidifier 16, such as an evaporator unit or chilled water fan coil, is configured to remove humidity from the air flow 12. The dehumidifier 16 may form part of a cooling unit, that also provides means to reduce the temperature of the air flow 12. The humidifier 17 may comprise a steam injector, or other humidifying device. The humidifier 17 is configured to provide humidity to the air flow 12. The heater 18 may comprise one or more heating elements, are configured to increase the temperature of the air flow 12. The cooling radiator 19 is configured to reduce the temperature of the air flow 12.

Figure 2:
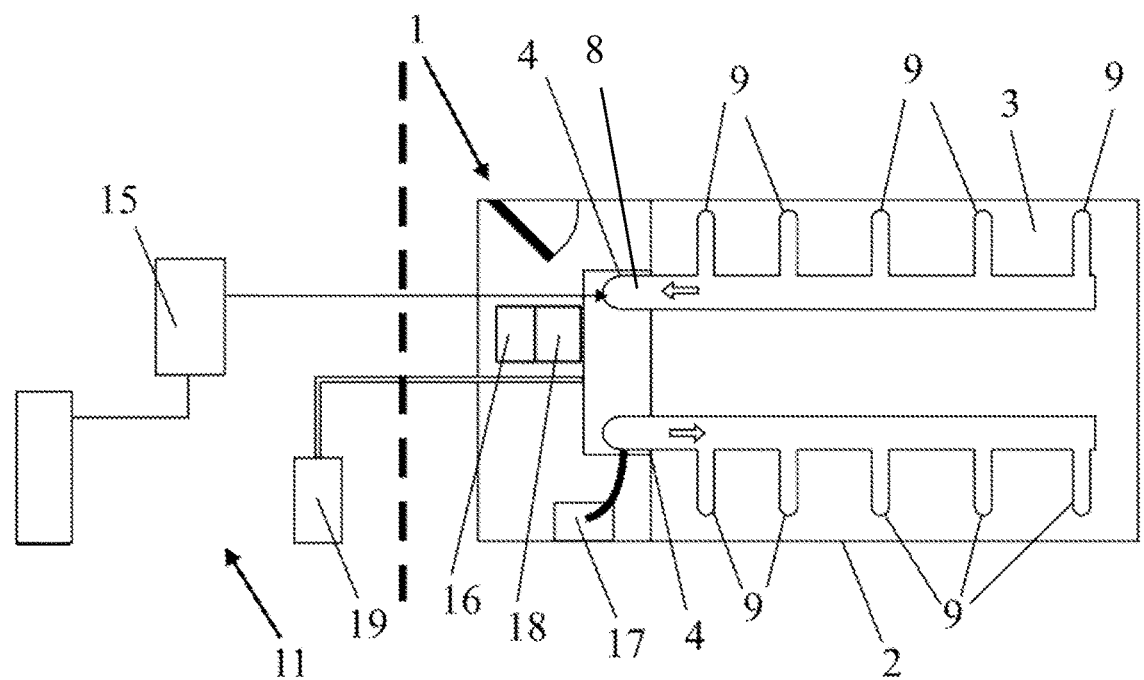
FIG. 2 shows the air conditioning assembly of FIG. 1 in plan view.
Figure 3:
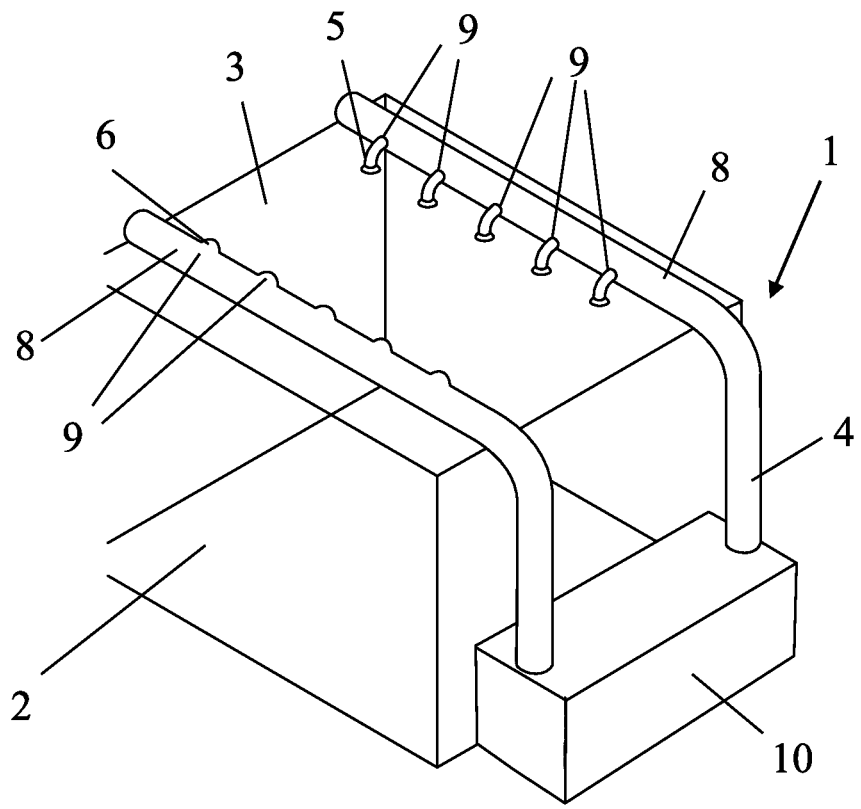
FIG. 3 shows the air handling unit and one embodiment of duct work, showing a pair of duct trunks, each one being operatively connected to a series of duct pipes.
Figure 4:
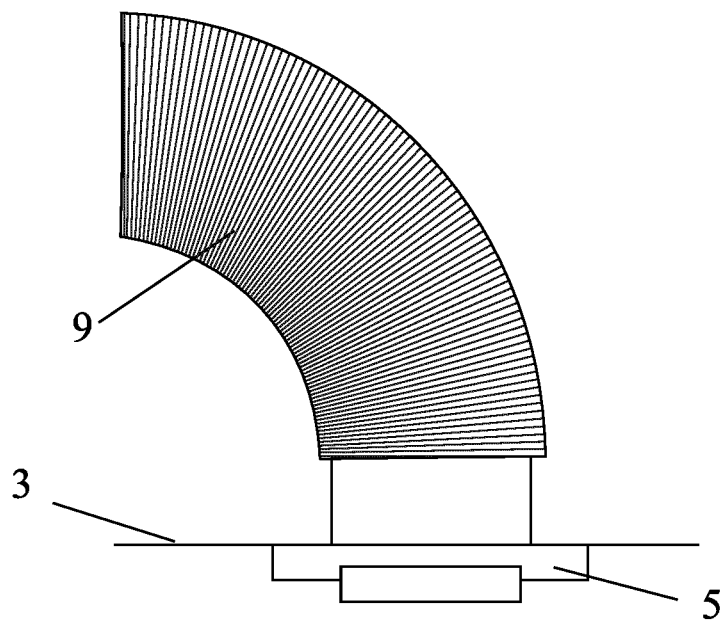
FIG. 4 shows one end of the duct pipe when mounted to a ceiling rose.

FIG. 2 shows the air conditioning assembly 1 of FIG. 1 in plan view where the air conditioning means 11, or the required units that make up the air conditioning means 11 specific to a required air flow, are configured external to the environmental chamber 2, and in fluid communication with the environmental chamber 2 through the duct work 4. The AHU 10 and/or one or more of the air conditioning means 11 may be located within a plant room, concealed behind a wall or space divider, thus keeping the environmental chamber 2 clutter free. FIG. 2 shows two duct trunks 8, one carrying air from the AHU 10 to the environmental chamber 2, and delivering this air through a series of five duct pipes 9, equally spaced along one side of the ceiling 3. The other duct trunk 8 draws air away from the environmental chamber 2, through a series of five duct pipes 9. The duct trunk 8 is of greater diameter to the duct pipes 9. The duct trunk 8 may comprise 305 mm ducting, whereas the duct pipes 9 may comprise 100 mm ducting. FIG. 3 shows the duct work 4 in more detail, and operatively connected to the AHU 10. The duct work 4 may comprise flexible ducting, and in particular the duct pipes 9 may comprise flexible ducting or a flexible material to relay the air flow 12 from the duct trunk 8 through the vents and into the environmental chamber 2, and likewise out of the environmental chamber 2. This flexible ducting helps to take the air flow 12 through a right angle, such that the duct pipes 9 can take the air flow 12 in a direction that is substantially perpendicular to the air flow 12 passing along the duct trunk 8. FIG. 4 shows an end of a duct pipe 9 entering through the vent in the ceiling 3 of the environmental chamber 2.

Figure 5:
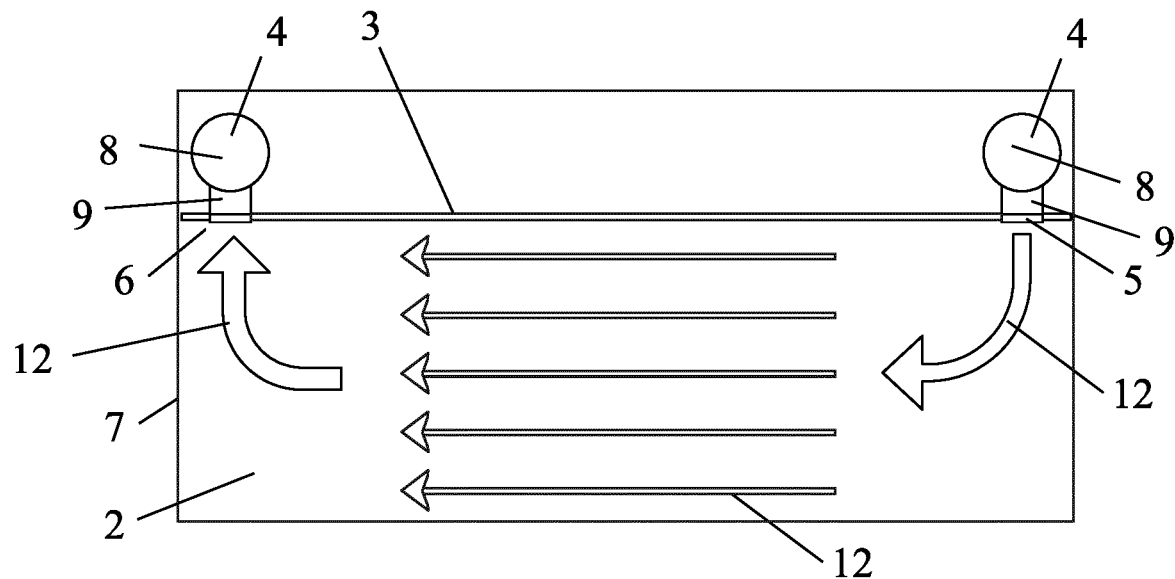
FIG. 5 shows a diagrammatic view of the air conditioning assembly of FIG. 1 in end view, showing laminar air flow through the environmental chamber; and, FIG. 6 shows one embodiment of control means housing a plurality of sensors.

FIG. 5 shows a side view of one arrangement of air conditioning assembly 1 in diagrammatic view, showing the air flow 12 entering the environmental chamber 2 through the plurality of inlet vents 5, and providing the environmental chamber 2 with substantially laminar air flow 12 throughout the chamber, before the air flow 12 exits through the plurality of outlet vents 6.

All of these air conditioning devices that make up the air conditioning means 11 are controlled by a control means 20. The control means 20 provides a way of controlling each of the devices set up within an environmental chamber 2 independently of each other where necessary, to create a required air flow 12 through the environmental chamber 2.

Figure 6:
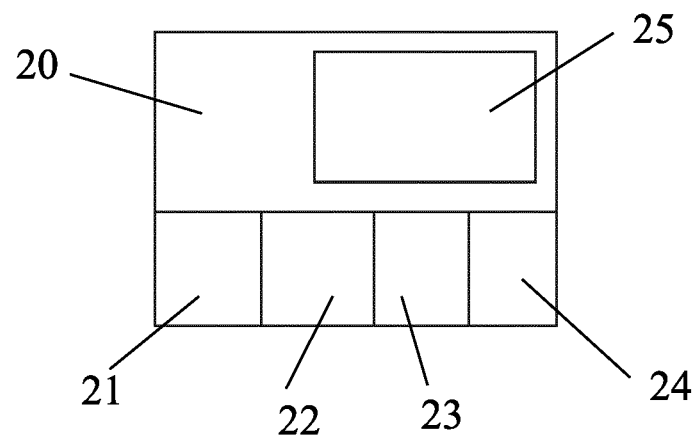

FIG. 6 shows one embodiment of control means 20, that wirelessly, or through hard wiring systems, provides the means of controlling the air conditioning means 11 within the plenum space 5. The control means 20 may be mounted to the walls 7 within the test space, may be outside of the environmental chamber 2, or may be within a portable device, not shown.

The control means 20 may also comprise a plurality of sensors, and therefore be mounted within a suitable location within the test space to take a valid reading of the air flow 12. The sensors may include any one or more of the following: oxygen sensor 21, temperature sensor 22, relative humidity sensor 23, carbon dioxide sensor 24 for sensing and storing or transmitting data for each of these. The control means 20 may incorporate a control panel 25 with button control means or touchscreen facility. A person conducting a test within the test space can therefore take a reading for any one of these, and control the air conditioning means 11 within the air conditioning assembly 1 accordingly.

In this specification, the verb "comprise" has its normal dictionary meaning, to denote non-exclusive inclusion. That is, use of the word "comprise" (or any of its derivatives) to include one feature or more, does not exclude the possibility of also including further features. The word "preferable" (or any of its derivatives) indicates one feature or more that is preferred but not essential.

All or any of the features disclosed in this specification (including any accompanying claims, abstract and drawings), and/or all or any of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An air conditioning assembly for an environmental chamber, the air conditioning assembly comprising:
    an air handling unit for supplying air to the environmental chamber;
    duct work in fluid communication with the air handing unit and in fluid communication with the environmental chamber; the duct work being configured to draw air from one side of the environmental chamber through at least two outlet vents, and to blow air into an opposite side of the environmental chamber through at least two equal but opposite inlet vents, whereby the outlet vents are spaced equidistant from one another and distributed evenly along one side of the environmental chamber, and the inlet vents are spaced equidistant from one another and distributed evenly along an opposite side of the environmental chamber, such that the outlet vents mirror the inlet vents; and,
    at least one air conditioning means in fluid communication with the air handling unit, configured to condition an air flow passing through said air handling unit;
    wherein, the at least one air conditioning means comprises an altitude simulator for changing oxygen content of the air flow, and the outlet vents and inlet vents are downwardly directed such that, in use, the inlet vents are configured to drive the air flow down a wall of the environmental chamber, and the outlet vents are configured to draw the air up an opposing wall of the environmental chamber, creating substantially laminar air flow throughout the environmental chamber.

2. The air conditioning assembly of claim 1, wherein the air conditioning means comprises a dehumidifier for reducing humidity of the air flow.

3. The air conditioning assembly of claim 1, wherein the air conditioning means comprises a humidifier for increasing the humidity of the air flow.

4. The air conditioning assembly of claim 1, wherein the air conditioning means comprises a heater to increase a temperature of the air flow.

5. The air conditioning assembly of claim 1, wherein the air conditioning means comprises a cooling radiator to reduce a temperature of the air flow.

6. The air conditioning assembly of claim 1, wherein the air conditioning assembly comprises at least one sensor selected from the following list of sensors: oxygen sensor, temperature sensor, humidity sensor, and carbon dioxide sensor.

7. The air conditioning assembly of claim 6, wherein the air conditioning assembly comprises at least one control means operatively connected to the at least one sensor.

8. The air conditioning assembly of claim 1, wherein the air conditioning assembly comprises at least one control means operatively connected to the air handling unit and the at least one air conditioning means.

9. The air conditioning assembly of claim 1, wherein the air conditioning assembly comprises flow directing means.

10. The air conditioning assembly of claim 1, wherein the duct work comprises an inlet duct trunk operatively connected to one end of at least two inlet duct pipes, arranged to draw air through each of the inlet vents, and the duct work comprises an outlet duct trunk operatively connected to one end of at least two outlet duct pipes, arranged to feed air through each of the outlet vents.

11. The air conditioning assembly of claim 1, wherein the inlet vents and outlet vents are within a ceiling of the environmental chamber.

12. The air conditioning assembly of claim 1, wherein the duct work comprises flexible ducting.

13. An environmental chamber incorporating the air conditioning assembly of claim 1.

14. A method of installing an air conditioning assembly in a room to form an environmental chamber, comprising the steps of:
    mounting an air handling unit outside the environmental chamber;
    installing duct work in fluid communication with the air handling unit and in fluid communication with the environmental chamber, the duct work being configured to draw air from one side of the environmental chamber through at least two outlet vents, and to blow air into an opposite side of the environmental chamber through at least two equal but opposite inlet vents, whereby the outlet vents are spaced equidistant from one another and distributed evenly along one side of the environmental chamber, and the inlet vents are spaced equidistant from one another and distributed evenly along an opposite side of the environmental chamber, such that the outlet vents mirror the inlet vents; and, installing at least one air conditioning means in fluid communication with the air handling unit, configured to condition an air flow passing through said air handling unit, wherein, the at least one air conditioning means comprises an altitude simulator for changing oxygen content of the air flow, and the outlet vents and inlet vents are downwardly directed such that, in use, the inlet vents are configured to drive air flow down a wall of the environmental chamber, and the outlet vents are configured to draw air up an opposing wall of the environmental chamber, creating substantially laminar air flow throughout the environmental chamber.

* * * * *